(12) United States Patent
Bressollier et al.

(10) Patent No.: US 8,691,773 B2
(45) Date of Patent: Apr. 8, 2014

(54) PEPTIDE COMPOUND WITH BIOLOGICAL ACTIVITY, ITS PREPARATION AND ITS APPLICATIONS

(75) Inventors: Philippe Bressollier, Limoges (FR); Maria Attilia Brugo, Antony (FR); Pascale Robineau, Antony (FR); Jean-Marie Schmitter, Champcevinel (FR); Maurice Sofeir, Antony (FR); Maria Camino Urdaci, Villenave d'Ornon (FR); Bernard Verneuil, Verneuil sur Vienne (FR)

(73) Assignee: Sanofi-Aventis SpA, Milan (IT)

( * ) Notice: Subject to any disclaimer, the term of this patent is extended or adjusted under 35 U.S.C. 154(b) by 765 days.

(21) Appl. No.: 12/245,841

(22) Filed: Oct. 6, 2008

(65) Prior Publication Data
US 2009/0312262 A1    Dec. 17, 2009

Related U.S. Application Data

(63) Continuation of application No. PCT/IB2007/002003, filed on Apr. 6, 2007.

(30) Foreign Application Priority Data

Apr. 6, 2006 (IT) ............................... MI2006A0678

(51) Int. Cl.
*A61K 38/00* (2006.01)
*C07K 16/00* (2006.01)

(52) U.S. Cl.
USPC ........................ 514/21.4; 514/2.3; 530/323

(58) Field of Classification Search
None
See application file for complete search history.

(56) References Cited

U.S. PATENT DOCUMENTS 7,354,888 B2 *   4/2008   Mostoller ..................... 510/111

FOREIGN PATENT DOCUMENTS

| EP | 1405641 | 4/2004 |
|---|---|---|
| WO | WO 98/56411 | 12/1998 |
| WO | WO 2004/026334 | 4/2004 |

OTHER PUBLICATIONS

Urdaci et al (J. Clin. Gasteroenterol. 38(Suppl 2):S86-90, Jul. 2004).*
Sahl, H-G, et. al., Lantibiotics: Biosynthesis and Biological Activites of Uniquely Modified Peptides from Gram-Positive Bacteria, Annu. Rev. Microbiol. (1998), vol. 52, pp. 41-79.
International Search Report for WO2007/113691 dated Oct. 11, 2007.

* cited by examiner

*Primary Examiner* — Patricia A Duffy
(74) *Attorney, Agent, or Firm* — Ronald G. Ort

(57) ABSTRACT

The invention relates to a peptide compound with biological activity, which in particular possesses antimicrobial properties, its preparation and its applications.

7 Claims, No Drawings

PEPTIDE COMPOUND WITH BIOLOGICAL ACTIVITY, ITS PREPARATION AND ITS APPLICATIONS

This application is a Continuation of International Application No. PCT/IB2007/002003, filed Apr. 6, 2007, which is incorporated herein by reference in its entirety.

FIELD OF THE INVENTION

The present invention relates to a peptide compound with biological activity, in particular possessing antimicrobial properties, to its preparation and to its applications.

BACKGROUND OF THE INVENTION

It is known that certain microorganisms, when administered live to humans or to animals, are capable of exerting a beneficial effect on the health of the host, in particular by producing antimicrobial substances.

Such organisms are generally called probiotic organisms.

Numerous studies have shown the beneficial effects, for humans or for animals, of these probiotic organisms, in particular in the treatment of gastrointestinal disorders, such as diarrhoea, acute diarrhoea, and diarrhoea associated with the use of medicinal drugs.

The probiotic organisms most studied to date are the lactic-acid bacteria, but it has also been reported that other live organisms can have a beneficial effect on health.

These other organisms include for example *Bacillus subtilis, Bacillus licheniformis, Bacillus coagulans, Bacillus cereus, Bacillus clausii, Bacillus polyfermentans*.

Among these, *Bacillus clausii* has been used for many years in a pharmaceutical composition marketed under the trade name Enterogermina®.

This pharmaceutical composition is intended in particular for combating gastrointestinal disorders and comprises a mixture of four strains of *Bacillus clausii*.

The antimicrobial biological activity of these probiotic organisms is generally linked to the natural production of compounds with antimicrobial activity, such as the lantibiotics. Thus, strains of *Bacillus clausii, Streptomyces mutans, Lactococcus lactis* produce respectively subtilin, mutacins and nisins, respectively.

Numerous antibiotics are used nowadays as therapeutic substances for the treatment of infectious diseases, but pathogens are becoming more and more resistant to the pharmaceuticals that are used. Some of them are already known to be "multi-resistant" and it is sometimes extremely difficult to treat the infections that they cause.

New molecules having antibiotic properties are therefore constantly being sought.

SUMMARY OF THE INVENTION

The purpose of the invention is to meet this demand, by proposing a compound with antimicrobial activity obtained from *Bacillus clausii*.

DETAILED DESCRIPTION OF THE INVENTION

A first object of the invention relates to a compound with antimicrobial activity.

A second object of the invention relates to a method for the preparation of the compound with antimicrobial activity of the invention.

A third object of the invention relates to a pharmaceutical composition containing the compound with antimicrobial activity of the invention.

A fourth object of the invention relates to the uses of the compound with antimicrobial activity of the invention.

According to a first aspect, the invention relates to a compound with antimicrobial activity.

Thus, a molecule produced by *Bacillus clausii*, and which displays antimicrobial activity, has been isolated and characterized.

The compound of the invention with antimicrobial activity is of a peptide nature and can be obtained from a culture of *Bacillus clausii* in a suitable medium up until sporulation, collection of the supernatant of the culture after centrifugation and filtration, and extraction of the fraction with antimicrobial activity.

The compound of the invention, which is mainly active against Gram-positive bacteria, can be obtained from *Bacillus clausii*, and has a molecular weight of 2107.5 Da, determined by mass spectrometry by the MALDI TOF and ESI method.

According to another characteristic, the compound of the invention is a lantibiotic, and has lanthionine bridges and modified amino acids in its peptide sequence.

According to one of its characteristics, the compound of the invention comprises the following sequence of amino acids and amino acid derivatives:

Phe-Dhb-Ala-Val-Dha-Phe-Ala-Abu-Pro-Gly-Ala-Gly-

Glu-Dhb-Gly-Ala-Phe-Asn-Ala-Phe-Ala in which
Dhb represents a didehydroaminobutyrate;
Dha represents a didehydroalanine;
Abu represents an aminobutyrate.

The compound of the invention possesses two lanthionine bridges, one between the alanine in position 3 and the alanine in position 7, and the other between the alanine in position 16 and the alanine in position 21.

A methyl-lanthionine bridge is moreover present between the aminobutyrate residue in position 8 and the alanine in position 11. A fourth bridge is present between the C-terminal amino-vinyl-cysteine group and the alanine residue in position 19.

Represented with the existing bridges, the compound of the invention has the following sequence:

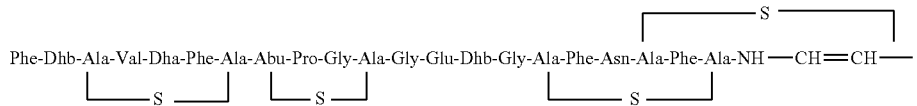

in which Dha, Dhb and Abu are as defined above.

According to a second aspect, the invention relates to a method for the preparation of the compound of the invention.

According to the invention, the compound of the invention can be extracted from *Bacillus clausii* according to the following method.

The method of preparation of the compound of the invention comprises the stages of:

culture of strains of *Bacillus clausii* in a suitable medium up until sporulation of the strains;

collection of the supernatant from the culture after centrifugation and filtration;

solid-phase extraction of the fraction obtained and elution.

If necessary, the fraction obtained, which corresponds to the molecule of the invention, can be purified by high-performance liquid chromatography (HPLC).

According to another embodiment, the compound of the invention can be prepared by conventional chemical synthesis, according to methods known to a person skilled in the art.

The compound of the invention displays antimicrobial activity against Gram-positive bacteria. In particular it has displayed antimicrobial activity against *S. aureus, Enterococcus faecium, Micrococcus* sp, *Lactococcus lactis, Clostridium difficile, Clostridium perfringens, Listeria monocytogenes* and the Gram-positive bacteria of the oral cavity.

Owing to its lantibiotic character, the compound of the invention can display a wider spectrum of biological activity, for example antiviral, antiparasitic or immunomodulating activity.

The compound of the invention can therefore be used for the preparation of medicinal products.

Thus, according to another of its aspects, the invention relates to medicinal products that contain the compound of the invention.

These medicinal products find application in therapy, in particular in the treatment and prevention of infectious diseases.

These medicinal products also find application in the treatment and/or prevention of intestinal disorders, for example in the treatment and prevention of intestinal dysbiosis and endogenous vitamin disorder, as well as in adjunctive treatment in the recovery of the intestinal microbial flora that has been altered as a result of antibiotic treatment or chemotherapy.

They also find application in the prevention and treatment of diarrhoea, in particular acute diarrhoea and diarrhoea associated with the use of medicinal products.

According to another of its aspects, the invention relates to pharmaceutical compositions comprising, as active principle, the compound according to the invention, for the treatment and/or prevention of the pathologies described above. These pharmaceutical compositions contain an effective dose of the compound according to the invention, as well as at least one pharmaceutically effective excipient.

Said excipients are selected, according to the pharmaceutical form and the desired route of administration, from the usual excipients that are known to a person skilled in the art.

In the pharmaceutical compositions of the present invention for oral, sublingual, subcutaneous, intramuscular, intravenous, topical, local, intratracheal, nasal, transdermal or rectal administration, the compound can be administered in dosage units, mixed with conventional pharmaceutical excipients, to animals and to humans for the prevention or for the treatment of the disorders or diseases mentioned above.

Appropriate dosage units comprise forms for the oral route such as tablets, soft or hard capsules, powders, granules and oral solutions or suspensions; sublingual, buccal, intratracheal, intraocular, nasal, and inhalation forms of administration; topical, transdermal, subcutaneous, intramuscular or intravenous forms of administration; rectal forms of administration, and implants. For topical application, compounds according to the invention can be used in creams, gels, ointments or lotions.

The composition of the invention can be administered by the most suitable route and at a dose that depends in particular on the nature of the infection, on the type of host in question, on the host's age, weight and general condition, on concomitant treatments being received, as well as on the host's response to the treatment and to the therapeutic rationale.

In general, for administration to humans, the composition is administered by the oral route in the form of a pharmaceutical composition of spores. For example, the dose can be of about $10 \times 10^9$ spores daily, for example from 1 to $8 \times 10^9$ spores daily, in particular 2, 4 or $6 \times 10^9$ spores daily, in a single dose or in several doses.

There may be special cases in which higher or lower doses are appropriate; such doses are still within the scope of the invention.

According to another of its aspects, the invention relates to the use of the compound of the invention for the preparation of a medicinal product intended for the prevention and/or treatment of the pathologies described above.

According to another of its aspects, the invention also relates to a method of treatment of the pathologies stated above that comprises the administration, to a patient, of an effective dose of the compound of the invention.

According to another of its aspects, the compound of the invention can also be used as an additive in cosmetic or foodstuff compositions.

According to this use, the compound of the invention is added in an amount sufficient to inhibit increase in bacterial growth in cosmetic or foodstuff compositions and thus permit their preservation.

The examples given below illustrate the invention though without limiting it.

EXAMPLES

1. Production of the Molecule

Production of the Supernatant.

An O/C strain of *Bacillus clausii* (obtained from the pharmaceutical composition marketed with the trade name Enterogermina®) is cultured for three days on Mueller Hinton medium at 37° C. and 180 rev/min until sporulation of the strain occurs.

The culture is then centrifuged and the supernatant is filtered with a membrane with pore size of 0.45 μm to remove any residual cells.

Extraction

The compound with antimicrobial activity is extracted in the solid phase on a Sep Pak plus $C_{18}$ cartridge (Waters). For this, 150 ml of supernatant obtained in the preceding stage is deposited on a cartridge and elution is performed with 100% methanol, after three successive washings with $NH_4HCO_3$ 25 mM, pH 8; $NH_4HCO_3$ 25 mM, pH 8+10% methanol and $NH_4HCO_3$ 25 mM, pH 8+50% methanol.

All of the active fractions eluted with 100% methanol are combined and concentrated by vacuum evaporation until a volume reduction factor of 10 is obtained.

The concentrate is stored at −20° C. No loss of activity was observed after 6 months of storage in these conditions.

Purification

Purification as far as homogenization of the substance extracted in the solid phase is performed by HPLC.

A first semi-preparative stage is carried out on a column $C_4$ Synchropack 100×8 mm. The fractions of eluate that display antimicrobial activity are collected and combined. The purity of the compound obtained at the end of this stage is greater than 80% and the yield in extraction—purification is about 6 mg-1$^{-1}$ of supernatant.

A second analytical stage is performed on a column $C_1$ Bischoff 150×4.6 mm. The fractions of eluate that display antimicrobial activity are collected and combined. The purity of the compound obtained at the end of this stage is greater than 90%.

2. Structural Investigation

Determination of Molecular Weight

The purified compound obtained in Example 1 above has a molecular weight of 2107.5 Da determined by mass spectrometry using the MALD TOF method and confirmed by mass spectrometry using the ESI method.

UV/Visible Absorption Spectrum

The compound of the invention absorbs in the ultraviolet and has in particular a peak at 265 nm compatible with the presence of aromatic amino acids in its structure.

Composition of the Amino Acids

After total hydrolysis with HCl 5.7 N, under vacuum, for 16 hours at 115° C. the presence of various amino acids is detected in the structure of the purified compound.

Investigation of the Various Enantiomeric Forms of the Amino Acids

The enantiomeric forms L and D of the amino acids that make up the sequence of the compound with antimicrobial activity were investigated after total acid hydrolysis, by derivatization with Nα-(2,4-dinitro-5-fluorophenyl)-L-alanine amide (Marfey's reagent) according to the method described by Szokan (J. Chromato., 1988, 444, pp. 115-122). The results indicate that all the residues of the amino acids that make up the antibiotic molecule are enantiomers of the L form.

Effects of Enzymatic or Chemical Treatments on Structure

The complete loss of activity following enzymatic treatment with Pronase confirms the peptide character of the new antibiotic compound.

Disulphide bridges are ruled out since a cistern-specific assay proved negative. In contrast, the presence of lanthionine bridges, sensitive to reducing treatment in an alkaline medium (Meyer, Anal. Biochem, 223, pp 185-190, 1994) can explain the loss of activity observed in the presence of β mercaptoethanol following structural modification, detected by reverse-phase HPLC. The drop, only partial, in activity measured at the end of less drastic treatment such as incubation at neutral pH in the presence of DTT 25 mM may be the result of specific reduction of the didehydro-amino acids present in the structure. These observations make it possible to formulate the hypothesis according to which the antimicrobial molecule produced by *Bacillus clausii* is a lantibiotic. This family of antibiotics is normally characterized by the presence of lanthionine bridges and modified amino acids in their structure.

Sequencing of the Native Molecule

Sequencing is performed using a Procise 492 A automatic sequencer (Applied Biosystem) by Edman recurrent degradation starting from the N-terminal end. The PTH amino acids formed are analysed by reverse-phase HPLC on a microbore C18 column. The sequencing of the antibiotic molecule, in the native state, is blocked at the end of the first step of Edman chemical degradation. The only residue identified corresponds to a phenylalanine which occupies the N-terminal position.

Sequencing of the Molecule After Chemical Modification

The information relating to the potential sequence of the novel antimicrobial substance produced by *Bacillus clausii*, deduced from the sequence of the encoding gene, combined with the information obtained from analysis of the amino acid composition and from the behaviour in the reducing medium reveal the presence of post-translational modifications characteristic of the lantibiotics.

The presence of didehydro-amino acids and of lanthionine bridges in the structure is at the origin of the blocking of sequencing of the molecule in the native state. The dehydroamino acids such as Dha (didehydroalanine) and Dhb (didehydroaminobutyrate) are deaminated during Edman chemical degradation and thus block the progress of the sequencing. These same residues Dha and Dhb are not detectable by analysis of the amino acid composition after total acid hydrolysis for the same reasons, and their deamination renders ineffective the reaction of derivatization with 6-aminoquinolyl-N-hydroxysuccinimidyl carbamate or with AQC (Waters), specific of the primary amine functions.

With the aim of overcoming the problems connected with the presence of modified amino acids and lanthionine bridges, a double chemical reaction was applied to the peptide antibiotic prior to its sequencing. The method employed was adapted from the work of Smith, Eur. J. Biochem. 2000, 267, p. 6810-6816. For this purpose, 50 nmol of the purified peptide is taken up in 10 µl of $H_2O$+4 mg of $NaBH_4$. 190 µl of a denaturing and antioxidant solution (570 mg of guanidine chloride+0.1 ml of N-ethylmorpholine, adjusted to pH 8.5 and to a final volume of 1 ml with $H_2O$) is added, then the reaction mixture is incubated in a stream of $N_2$ for 72 hours at 37° C.

This treatment specifically reduces the didehydro-amino acids without affecting the lanthionine bridges.

The peptide thus reduced is recovered on a Prosorb column (Perkin Elmer) equipped with a PVDF membrane. After washing the membrane with 200 µl of 0.1% TFA, the peptide absorbed on this support is submitted to a second reduction in the presence of ethanethiol (addition of 20 µl of a solution comprising 280 µl of methanol+200 µl of $H_2O$+65 ml of NaOH+60 µl of ethanethiol) for one hour at 50° C.

Covalent Structure of the Antibiotic Molecule Produced with *Bacillus Clausii*

The covalent structure is in agreement with all of the data obtained. The molecular weight calculated on the basis of the masses of the mono-isotopic residues is 2107.5 Da. The antimicrobial molecule secreted by *Bacillus clausii* s a lantibiotic possessing 4 lanthionine bridges and methyllanthionine as well as 3 didehydro-amino acid residues in its structure. The structure is in agreement with the mass found, 2107.5 Da, with the results obtained after performing chemical modifications on the molecule, and with the amino acid sequence deduced on the basis of the gene that codes for its production, found in *B. clausii*. The structure was confirmed by NMR analysis.

The other three strains (N/R, SIN, T) of *Bacillus clausii* present in the pharmaceutical composition Enterogermina® displayed the same profile of antimicrobial activity as the O/C strain.

We claim:

1. A purified peptide compound comprising the following amino acid sequence:

```
Phe-Dhb-Ala-Val-Dha-Phe-Ala-Abu-Pro-Gly-Ala-Gly-
Glu-Dhb-Gly-Ala-Phe-Asn-Ala-Phe-Ala
``` wherein:
Dhb represents a didehydroaminobutyrate;
Dha represents a didehydroalanine; and
Abu represents an aminobutyrate,
wherein the purity is greater than 90%.

2. The peptide compound according to claim 1, which has two lanthionine bridges, one between the alanine in position 3 and the alanine in position 7, and the other between the alanine in position 16 and the alanine in position 21; a methyl-lanthionine bridge between the aminobutyrate residue in position 8 and the alanine in position 11; and a fourth bridge between the C-terminal amino-vinyl-cysteine group and the residue of the alanine in position 19.

3. The peptide compound according to claim 1, wherein the amino acid residues are enantiomers of the L form.

4. A pharmaceutical composition comprising the peptide compound according to claim 1, and at least one pharmaceutically acceptable excipient.

5. A pharmaceutical composition comprising the peptide compound according to claim 2, and at least one pharmaceutically acceptable excipient.

6. A pharmaceutical composition comprising the peptide compound according to claim 3, and at least one pharmaceutically acceptable excipient.

7. The purified peptide compound according to claim 1, which has a molecular weight of about 2107.5 Da.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Bacillus clausii

```
<220> FEATURE:
<221> NAME/KEY: MISC_FEATURE
<222> LOCATION: (2)..(2)
<223> OTHER INFORMATION: didehydroaminobutyrate
<220> FEATURE:
<221> NAME/KEY: THIOETH
<222> LOCATION: (3)..(7)
<220> FEATURE:
<221> NAME/KEY: MISC_FEATURE
<222> LOCATION: (5)..(5)
<223> OTHER INFORMATION: didehydroalanine
<220> FEATURE:
<221> NAME/KEY: BINDING
<222> LOCATION: (8)..(11)
<223> OTHER INFORMATION: methyl-lanthionine bridge
<220> FEATURE:
<221> NAME/KEY: MISC_FEATURE
<222> LOCATION: (8)..(8)
<223> OTHER INFORMATION: Abu
<220> FEATURE:
<221> NAME/KEY: MISC_FEATURE
<222> LOCATION: (13)..(13)
<223> OTHER INFORMATION: Glu
<220> FEATURE:
<221> NAME/KEY: MISC_FEATURE
<222> LOCATION: (14)..(14)
<223> OTHER INFORMATION: didehydroaminobutyrate
<220> FEATURE:
<221> NAME/KEY: THIOETH
<222> LOCATION: (16)..(21)
<220> FEATURE:
<221> NAME/KEY: MISC_FEATURE
<222> LOCATION: (18)..(18)
<223> OTHER INFORMATION: Asn
<220> FEATURE:
<221> NAME/KEY: BINDING
<222> LOCATION: (19)..(21)
<223> OTHER INFORMATION: bridge between alanine residue 19 and amino
      vinyl cystein group at C-terminus

<400> SEQUENCE: 1

Phe Xaa Ala Val Xaa Phe Ala Xaa Pro Gly Ala Gly Glx Xaa Gly Ala
1               5                   10                  15

Phe Asx Ala Phe Ala
            20
```